United States Patent
Nishide et al.

(10) Patent No.: US 7,379,526 B2
(45) Date of Patent: May 27, 2008

(54) X-RAY CT APPARATUS AND X-RAY CT IMAGING METHOD

(75) Inventors: Akihiko Nishide, Tokyo (JP); Akira Hagiwara, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 11/266,534

(22) Filed: Nov. 3, 2005

(65) Prior Publication Data

US 2006/0093083 A1 May 4, 2006

(30) Foreign Application Priority Data

Nov. 4, 2004 (JP) ............... 2004-320263

(51) Int. Cl.
*G01N 23/00* (2006.01)
(52) U.S. Cl. .......................... 378/17; 378/15
(58) Field of Classification Search ............... 378/15, 378/17, 4, 13, 14
See application file for complete search history.

(56) References Cited

U.S. PATENT DOCUMENTS

| 4,734,988 A | 4/1988 | Steele et al. |
| 6,466,640 B1 * | 10/2002 | Taguchi .................. 378/15 |
| 6,845,144 B2 | 1/2005 | Nishide et al. |
| 6,865,247 B2 | 3/2005 | Hagiwara |
| 6,873,679 B2 | 3/2005 | Hagiwara |
| 7,006,591 B2 * | 2/2006 | Machida .................. 378/4 |
| 2003/0016781 A1 | 1/2003 | Huang |
| 2004/0081273 A1 | 4/2004 | Ning |
| 2004/0086075 A1 * | 5/2004 | Hein et al. .............. 378/4 |

FOREIGN PATENT DOCUMENTS

| JP | 2002-320609 | 11/2002 |
| JP | 2003-159244 | 6/2003 |
| JP | 2003-334188 | 11/2003 |
| JP | 2004-041674 | 2/2004 |
| JP | 2004-041675 | 2/2004 |
| JP | 2004-073360 | 3/2004 |

\* cited by examiner

*Primary Examiner*—Hoon Song
(74) *Attorney, Agent, or Firm*—Armstrong Teasdale LLP

(57) ABSTRACT

The present invention aims to reduce exposure at a helical scan in an X-ray CT apparatus using an X-ray area detector typified by a multi-row X-ray detector or a flat panel. When the angle of an X-ray cone beam spread in a z direction is assumed to be Acone, a scanning gantry is tilted by Acone/2 to start X-ray irradiation/data acquisition of the helical scan, after which the X-ray irradiation/data acquisition is completed at the number of revolutions corresponding to "integral number n+0.5".

26 Claims, 10 Drawing Sheets

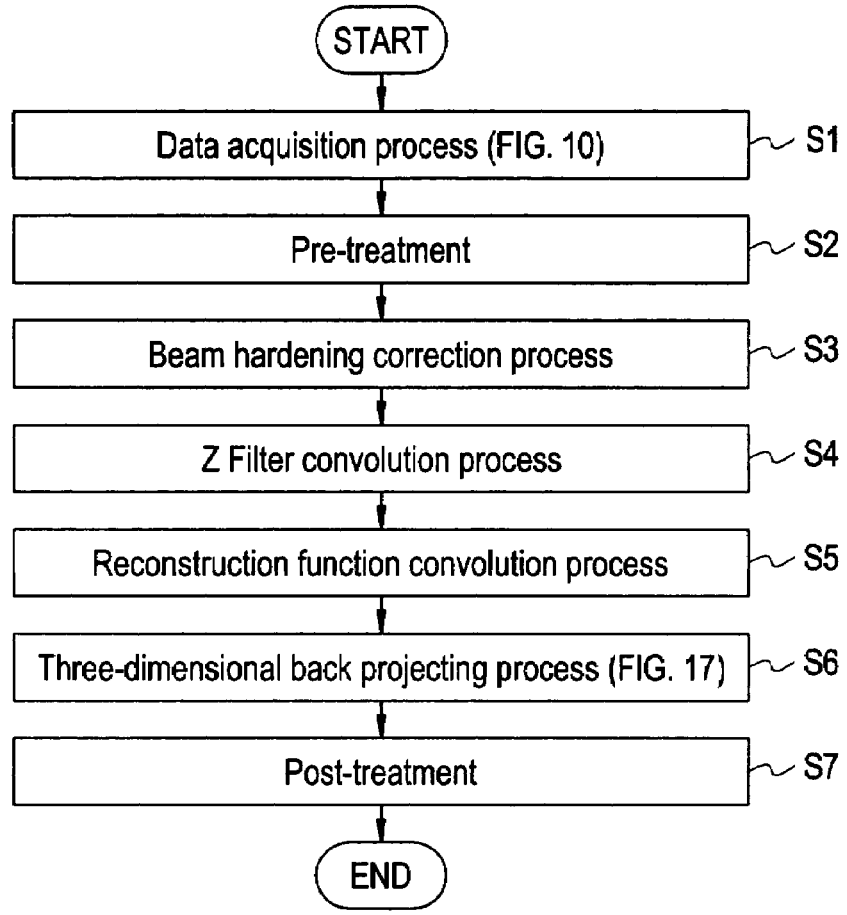

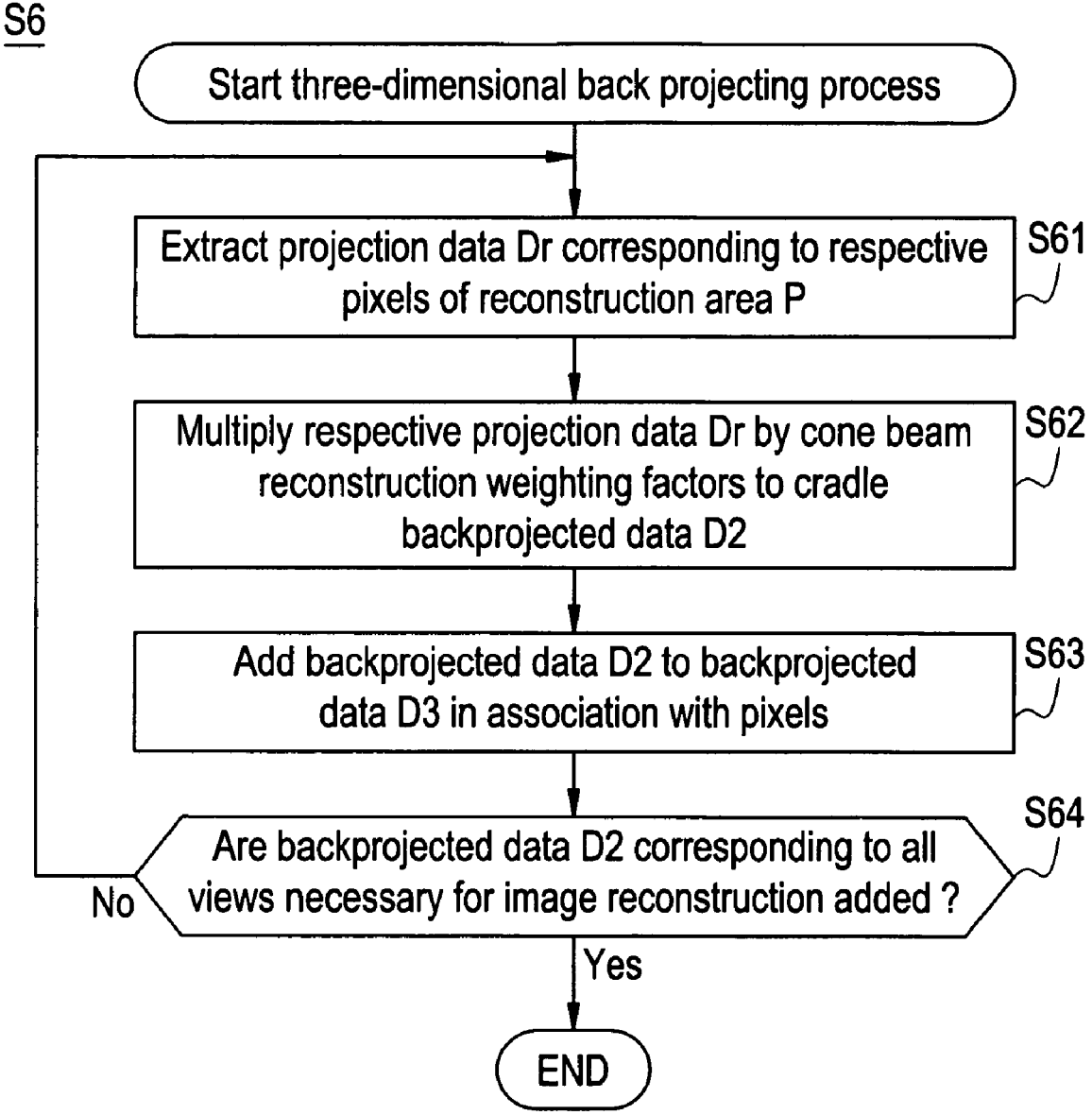

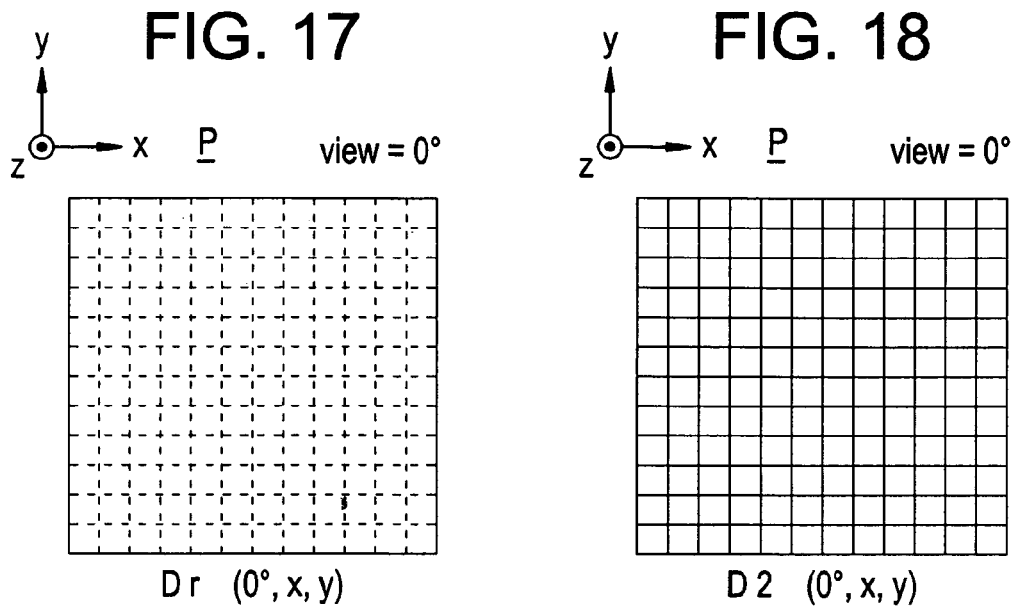
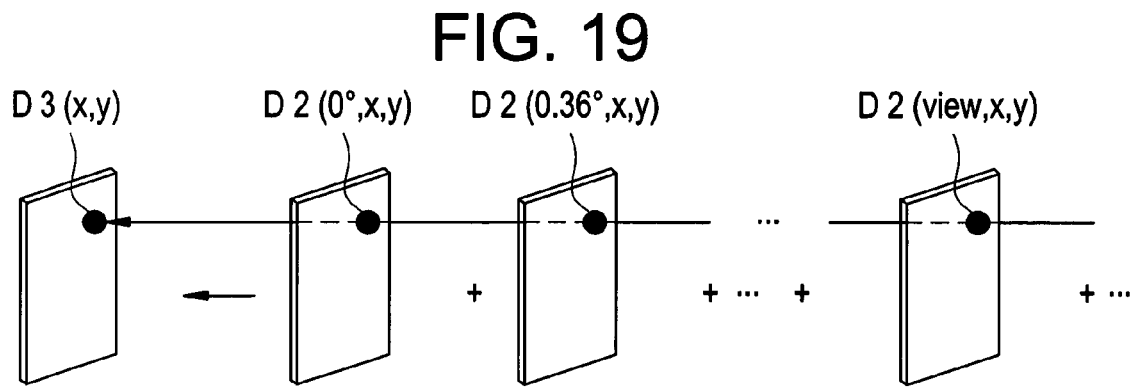
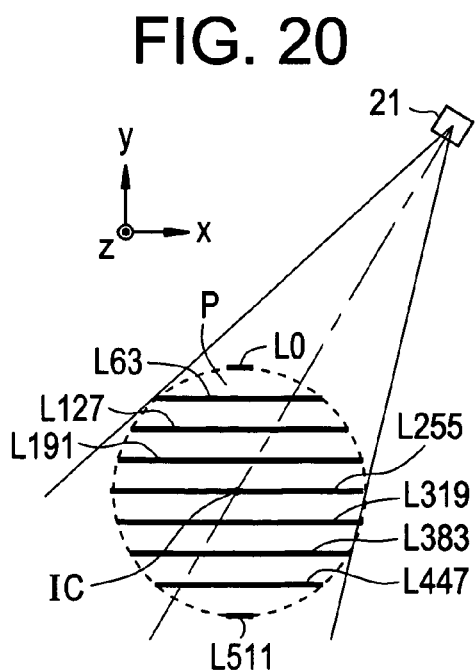

X-RAY CT APPARATUS AND X-RAY CT IMAGING METHOD

CROSS REFERENCE TO RELATED APPLICATIONS

This application claims the benefit of Japanese Application No. 2004-320263 filed Nov. 4, 2004.

BACKGROUND OF THE INVENTION

The present invention relates to an X-ray CT (Computed Tomography) apparatus and an X-ray CT imaging method, and more specifically to an X-ray CT apparatus and an X-ray CT imaging method both having no needless X-ray irradiation and capable of reducing an exposure range of a subject at a helical scan (including a variable pitch helical scan or a variable speed helical scan).

There has heretofore been known an X-ray CT apparatus wherein when a helical scan is performed, a collimator located on the front side as viewed in a linearly-moved direction of the helical scan restricts the position of an end surface of an X-ray cone beam on the front side as viewed in the linearly-moved direction at the start of X-ray irradiation in order to prevent exposure of the front side as viewed in the linearly-moved direction rather than a linearly-moved range in which one desires to collect projection data, and the collimator located on the rear side as viewed in the linearly-moved direction restricts the position of an end surface of the X-ray cone beam on the rear side as viewed in the linearly-moved direction at the completion of the X-ray irradiation in order to prevent exposure of the rear side as viewed in the linearly-moved direction rather than the linearly-moved range in which one desires to collect the projection data (refer to, for example, a patent document 1).

[Patent Document 1] Japanese Patent Publication Laid-Open No. 2002-320609

In the conventional X-ray CT apparatus, an X-ray spread to the front side as viewed in the linearly-moved direction rather than the linearly-moved range in which one desires to collect the projection data, is shielded or blocked by the collimator, and an X-ray spread to the rear side as viewed in the linearly-moved direction rather than the linearly-moved range in which one desires to collect the projection data, is shielded by the collimator, thus reducing an exposure range of a subject at the helical scan.

However, a problem arises in that the X-ray at each shielded portion results in needless X-ray irradiation. It is also difficult to perform the collimator control with satisfactory accuracy by real-time control. There is a possibility that an error in X-ray irradiation will occur due to a control error. Hence problems associated with image quality and needless exposure have arisen.

SUMMARY OF THE INVENTION

Therefore, an object of the present invention is to provide an X-ray CT apparatus and an X-ray CT imaging method both having no needless X-ray irradiation and capable of reducing an exposure range of a subject at a helical scan. Here, the helical scan includes a variable pitch helical scan or a variable speed helical scan.

In a first aspect, the present invention provides an X-ray CT apparatus comprising an X-ray area detector typified by an X-ray CT apparatus with a multi-row X-ray detector, or a flat panel; and scanning gantry tilting means which tilts a scanning gantry in such a manner that X-ray irradiation is started in a state in which an end surface of an X-ray cone beam on a front side as viewed in a linearly-moved direction of a helical scan is rendered horizontal or substantially horizontal to a reconstruction area.

In the X-ray CT apparatus according to the first aspect, when, for example, the reconstruction area is orthogonal to the linearly-moved direction, the end surface on the front side as viewed in the linearly-moved direction, of the X-ray cone beam at the start of the X-ray irradiation is set vertical or substantially vertical to the linearly-moved direction owing to the scanning gantry being tilted. Thus, since an X-ray is not spread to the front side as viewed in the linearly-moved direction than a linearly-moved range in which one desires to collect projection data, an exposure range of a subject at the helical scan can be reduced. Since no X-ray cone beam is shielded, needless X-ray irradiation is not made either.

In a second aspect, the present invention provides an X-ray CT apparatus comprising an X-ray area detector typified by an X-ray CT apparatus with a multi-row X-ray detector, or a flat panel; and X-ray irradiating means which forms an X-ray cone beam in such a manner that X-ray irradiation is started in a state in which an end surface of an X-ray cone beam on a front side as viewed in a linearly-moved direction of a helical scan is set vertical or substantially vertical.

In the X-ray CT apparatus according to the second aspect, when a reconstruction area is vertical to the linearly-moved direction, the end surface on the front side as viewed in the linearly-moved direction, of the X-ray cone beam at the start of the X-ray irradiation becomes parallel or substantially parallel to the reconstruction area. Thus, since an X-ray is not spread to the front side as viewed in the linearly-moved direction than a linearly-moved range in which one desires to collect projection data, it is possible to reduce an exposure range of a subject at the helical scan. Since no X-ray cone beam is shielded, needless X-ray irradiation is not done either.

In a third aspect, the present invention provides an X-ray CT apparatus comprising an X-ray area detector typified by an X-ray CT apparatus with a multi-row X-ray detector, or a flat panel; and X-ray irradiation control means which controls X-ray irradiation in such a manner that the number of revolutions during an X-ray irradiation period at a helical scan reaches "n+Δn" (where n: integral number and Δn: decimal number).

In the X-ray CT apparatus according to the third aspect, since the number of revolutions for rotating a scanning gantry with the X-ray irradiation is not an integral number of revolutions, an end surface of an X-ray cone beam on the front side as viewed in a linearly-moved direction at the start of the X-ray irradiation and an end surface of the X-ray cone beam on the rear side as viewed in the linearly-moved direction at the completion of the X-ray irradiation can be made close to each other in parallel. Therefore, no X-ray is spread to an unnecessary range at the start of the X-ray irradiation or the completion of the X-ray irradiation, and hence an exposure range of a subject at the helical scan can be reduced. Since no X-ray cone beam is shielded, needless X-ray irradiation is not done either.

In a fourth aspect, the present invention provides an X-ray CT apparatus comprising an X-ray area detector typified by an X-ray CT apparatus with a multi-row X-ray detector, or a flat panel; scanning gantry tilting means which tilts a scanning gantry upon a helical scan; and X-ray irradiation control means which controls X-ray irradiation in such a manner that the number or revolutions during an X-ray irradiation period at the helical scan reaches "n+Δn" (where n: integral number and Δn: decimal number).

In the X-ray CT apparatus according to the fourth aspect, when, for example, a reconstruction area is vertical to a linearly-moved direction, an end surface on the front side as viewed in the linearly-moved direction, of an X-ray cone beam can be set vertical or substantially vertical to the linearly-moved direction by tilting the scanning gantry. Thus, since an X-ray is not spread to the front side as viewed in the linearly-moved direction than a linearly-moved range in which one desires to collect projection data, an exposure range of a subject at the helical scan can be reduced. Since the number of revolutions for rotating the scanning gantry with the X-ray irradiation is not an integral number of revolutions, an end surface of the X-ray cone beam on the front side as viewed in the linearly-moved direction at the start of the X-ray irradiation and an end surface of the X-ray cone beam on the rear side as viewed in the linearly-moved direction at the completion of the X-ray irradiation can be made close to each other in parallel. Therefore, no X-ray is spread to an unnecessary range at the start of the X-ray irradiation or the completion of the X-ray irradiation, and hence the exposure range of the subject at the helical scan can be reduced. Since no X-ray cone beam is shielded, needless X-ray irradiation is not done either.

In a fifth aspect, the present invention provides an X-ray CT apparatus having above configuration, wherein when an X-ray cone beam angle spread in the linearly-moved direction is assumed to be Acone, the scanning gantry is tilted by Acone/2 or an angle close thereto.

In the X-ray CT apparatus according to the fifth aspect, the scanning gantry is tilted by Acone/2 or the angle close thereto to set an end surface on the front side as viewed in the linearly-moved direction, of the X-ray cone beam vertical or substantially vertical to the linearly-moved direction. Therefore, when a reconstruction area is vertical to the linearly-moved direction, no X-ray is spread to the font side as viewed in the linearly-moved direction than a linearly-moved range in which one desires to collect projection data. It is therefore possible to reduce an exposure range of a subject at a helical scan.

In a sixth aspect, the present invention provides an X-ray CT apparatus having above configuration, wherein Δn=0.5 or a value close thereto.

In the X-ray CT apparatus according to the sixth aspect, since the number of revolutions for allowing a scanning gantry to rotate with X-ray irradiation is set to an integral number of revolutions+a half-turn or a value close thereto, an end surface of an X-ray cone beam on the front side as viewed in a linearly-moved direction at the start of the X-ray irradiation and an end surface of the X-ray cone beam on the rear side as viewed in the linearly-moved direction at the completion of the X-ray irradiation can be made parallel or substantially parallel. Therefore, no X-ray is spread to an unnecessary range at the start of the X-ray irradiation or the completion of the X-ray irradiation, and hence an exposure range of a subject at a helical scan can be reduced.

In a seventh aspect, the present invention provides an X-ray CT apparatus having above configuration, further comprising three-dimensional image reconstructing (X-ray cone beam image reconstructing) means.

In the X-ray CT apparatus according to the seventh aspect, the three-dimensional image reconstruction (X-ray cone beam image reconstruction) is used. Thus, even when the scanning gantry is tilted, a tomogram in an xy plane, i.e., a plane vertical to a z axis (axis as viewed in a linearly-moved direction) can be obtained in good image quality less reduced in artifact. An image with good image quality less reduced in artifact can be obtained at an arbitrary position in an X-ray irradiation range as viewed in the linearly-moved direction.

In an eighth aspect, the present invention provides an X-ray CT apparatus comprising an X-ray area detector typified by an X-ray CT apparatus with a multi-row X-ray detector, or a flat panel; and scanning gantry tilting means which tilts a scanning gantry in such a manner that X-ray irradiation is completed in a state in which an end surface of an X-ray cone beam on the rear side as viewed in a linearly-moved direction of a helical scan is set parallel or substantially parallel to a reconstruction area.

In the X-ray CT apparatus according to the eighth aspect, when, for example, the reconstruction area is orthogonal to the linearly-moved direction, the end surface on the rear side as viewed in the linearly-moved direction, of the X-ray cone beam at the completion of the X-ray irradiation is set vertical or substantially vertical to the linearly-moved direction owing to the scanning gantry being tilted. Thus, since an X-ray is not spread to the rear side as viewed in the linearly-moved direction than a linearly-moved range in which one desires to collect projection data, an exposure range of a subject at the helical scan can be reduced. Since no X-ray cone beam is shielded, needless X-ray irradiation is not made either.

In a ninth aspect, the present invention provides an X-ray CT apparatus comprising an X-ray area detector typified by an X-ray CT apparatus with a multi-row X-ray detector, or a flat panel; scanning gantry tilting means which tilts a scanning gantry in such a manner that X-ray irradiation is started in a state in which an end surface of an X-ray cone beam on the front side as viewed in a linearly-moved direction of a helical scan is set parallel or substantially parallel to a reconstruction area; and X-ray irradiation control means which controls X-ray irradiation in a such a manner that the X-ray irradiation is completed at such a number of revolutions that an end surface of the X-ray cone beam on the rear side as viewed in the linearly-moved direction of the helical scan becomes parallel or substantially parallel to the reconstruction area.

In the X-ray CT apparatus according to the ninth aspect, when, for example, the reconstruction area is vertical to the linearly-moved direction, the end surface on the front side as viewed in the linearly-moved direction, of the X-ray cone beam at the start of the X-ray irradiation is set vertical or substantially vertical to the linearly-moved direction owing to the scanning gantry being tilted. When, for example, the reconstruction area is vertical to the linearly-moved direction, the X-ray irradiation is completed at such an unintegral number of revolutions that the end surface on the rear side as viewed in the linearly-moved direction, of the X-ray cone beam at the completion of the X-ray irradiation becomes vertical or substantially vertical to the linearly-moved direction. Thus, no X-ray is spread to an unnecessary range at the start of the X-ray irradiation or the completion of the X-ray irradiation, and hence an exposure range of a subject at the helical scan can be reduced. Since the X-ray cone beam is not shielded, needless X-ray irradiation is not done either.

In a tenth aspect, the present invention provides an X-ray CT apparatus according to any of the first through ninth aspects, further comprising helical scan means which performs a variable pitch helical scan or a variable speed helical scan.

In the above constitution, the variable pitch helical scan or the variable speed helical scan is a helical scan which collects or acquires image reconstruction data even at the start of a linear movement and the completion thereof, and even in acceleration or deceleration in its mid course.

In the X-ray CT apparatus according to the tenth aspect, the variable pitch helical scan or the variable speed helical scan provides or produces a low speed upon the start or completion of the linear movement. Therefore, the image quality of a portion equivalent to its start or completion is improved as compared with the case of a constant pitch helical scan or a constant speed helical scan.

In an eleventh aspect, the present invention provides an X-ray CT imaging method using an X-ray area detector typified by a multi-row X-ray detector or a flat panel, comprising tilting a scanning gantry in such a manner that X-ray irradiation is started in a state in which an end surface of an X-ray cone beam on the front side as viewed in a linearly-moved direction of a helical scan is set parallel or substantially parallel to a reconstruction area.

In the X-ray CT imaging method according to the eleventh aspect, when, for example, the reconstruction area is vertical to the linearly-moved direction, the end surface on the front side as viewed in the linearly-moved direction, of the X-ray cone beam at the start of the X-ray irradiation is set vertical or substantially vertical to the linearly-moved direction owing to the scanning gantry being tilted. Consequentially, since an X-ray is not spread to the front side as viewed in the linearly-moved direction than a linearly-moved range in which one desires to collect projection data, an exposure range of a subject at the helical scan can be reduced. Since no X-ray cone beam is shielded, needless X-ray irradiation is not made either.

In a twelfth aspect, the present invention provides an X-ray CT imaging method using an X-ray area detector typified by a multi-row X-ray detector or a flat panel, comprising forming an X-ray cone beam in such a manner that X-ray irradiation is started in a state in which an end surface of the X-ray cone beam on the front side as viewed in a linearly-moved direction of a helical scan is set vertical or substantially vertical.

In the X-ray CT imaging method according to the twelfth aspect, when a reconstruction area is vertical to the linearly-moved direction, the end surface on the front side as viewed in the linearly-moved direction, of the X-ray cone beam at the start of the X-ray irradiation becomes parallel or substantially parallel to the reconstruction area. Thus, since an X-ray is not spread to the front side as viewed in the linearly-moved direction than a linearly-moved range in which one desires to collect projection data, it is possible to reduce an exposure range of a subject at the helical scan. Since no X-ray cone beam is shielded, needless X-ray irradiation is not done either.

In a thirteenth aspect, the present invention provides an X-ray CT imaging method using an X-ray area detector typified by a multi-row X-ray detector or a flat panel, comprising controlling X-ray irradiation in such a manner that the number of revolutions during an X-ray irradiation period at a helical scan reaches "n+Δn" (where n: integral number and Δn: decimal number).

In the X-ray CT imaging method according to the thirteenth aspect, since the number of revolutions for rotating a scanning gantry with the X-ray irradiation is not an integral number of revolutions, an end surface of an X-ray cone beam on the front side as viewed in a linearly-moved direction at the start of the X-ray irradiation and an end surface of the X-ray cone beam on the rear side as viewed in the linearly-moved direction at the completion of the X-ray irradiation can be made close to each other in parallel. Therefore, no X-ray is spread to an unnecessary range at the start of the X-ray irradiation or the completion of the X-ray irradiation, and hence an exposure range of a subject at the helical scan can be reduced. Since no X-ray cone beam is shielded, needless X-ray irradiation is not done either.

In a fourteenth aspect, the present invention provides an X-ray CT imaging method using an X-ray area detector typified by a multi-row X-ray detector or a flat panel, comprising tilting a scanning gantry upon a helical scan; and controlling X-ray irradiation in such a manner that the number or revolutions during an X-ray irradiation period at the helical scan reaches "n+Δn" (where n: integral number and Δn: decimal number).

In the X-ray CT imaging method according to the fourteenth aspect, when, for example, a reconstruction area is vertical to a linearly-moved direction, an end surface on the front side as viewed in the linearly-moved direction, of an X-ray cone beam can be set vertical or substantially vertical to the linearly-moved direction by tilting the scanning gantry. Thus, since an X-ray is not spread to the front side as viewed in the linearly-moved direction than a linearly-moved range in which one desires to collect projection data, an exposure range of a subject at the helical scan can be reduced. Since the number of revolutions for rotating the scanning gantry with the X-ray irradiation is not an integral number of revolutions, an end surface of the X-ray cone beam on the front side as viewed in the linearly-moved direction at the start of the X-ray irradiation and an end surface of the X-ray cone beam on the rear side as viewed in the linearly-moved direction at the completion of the X-ray irradiation can be made close to each other in parallel. Therefore, no X-ray is spread to an unnecessary range at the start of the X-ray irradiation or the completion of the X-ray irradiation, and hence the exposure range of the subject at the helical scan can be reduced. Since no X-ray cone beam is shielded, needless X-ray irradiation is not done either.

In a fifteenth aspect, the present invention provides an X-ray CT imaging method having above configuration, wherein when an X-ray cone beam angle spread in a linearly-moved direction is assumed to be Acone, a scanning gantry is tilted by Acone/2 or an angle close thereto.

In the X-ray CT imaging method according to the fifteenth aspect, the scanning gantry is tilted by Acone/2 or the angle close thereto to set an end surface on the front side as viewed in the linearly-moved direction, of the X-ray cone beam vertical or substantially vertical to the linearly-moved direction. Therefore, when a reconstruction area is vertical to the linearly-moved direction, no X-ray is spread to the font side as viewed in the linearly-moved direction than a linearly-moved range in which one desires to collect projection data. It is therefore possible to reduce an exposure range of a subject at a helical scan.

In a sixteenth aspect, the present invention provides an X-ray CT imaging method having above configuration, wherein Δn=0.5 or a value close thereto.

In the X-ray CT imaging method according to the sixteenth aspect, since the number of revolutions for allowing a scanning gantry to rotate with X-ray irradiation is set to an integral number of revolutions+a half-turn or a value close thereto, an end surface of an X-ray cone beam on the front side as viewed in a linearly-moved direction at the start of the X-ray irradiation and an end surface of the X-ray cone beam on the rear side as viewed in the linearly-moved direction at the completion of the X-ray irradiation can be made parallel or substantially parallel. Therefore, no X-ray is spread to an unnecessary range at the start of the X-ray irradiation or the completion of the X-ray irradiation, and hence an exposure range of a subject at a helical scan can be reduced.

In a seventeenth aspect, the present invention provides an X-ray CT imaging method having above configuration, wherein a three-dimensional image reconstruction (X-ray cone beam image reconstruction) is used for an image reconstruction.

In the X-ray CT imaging method according to the seventeenth aspect, the three-dimensional image reconstruction (X-ray cone beam image reconstruction) is used. Thus, even when the scanning gantry is tilted, a tomogram in an xy plane, i.e., a plane vertical to a z axis (axis as viewed in a linearly-moved direction) can be obtained in good image quality less reduced in artifact. An image with good image quality less reduced in artifact can be obtained at an arbitrary position in an X-ray irradiation range as viewed in the linearly-moved direction.

In an eighteenth aspect, the present invention provides an X-ray CT imaging method using an X-ray area detector typified by a multi-row X-ray detector or a flat panel, comprising tilting a scanning gantry in such a manner that X-ray irradiation is completed in a state in which an end surface of an X-ray cone beam on the rear side as viewed in a linearly-moved direction of a helical scan is set parallel or substantially parallel to a reconstruction area.

In the X-ray CT imaging method according to the eighteenth aspect, when, for example, the reconstruction area is orthogonal to the linearly-moved direction, the end surface on the rear side as viewed in the linearly-moved direction, of the X-ray cone beam at the completion of the X-ray irradiation is set vertical or substantially vertical to the linearly-moved direction owing to the scanning gantry being tilted. Thus, since an X-ray is not spread to the rear side as viewed in the linearly-moved direction than a linearly-moved range in which one desires to collect projection data, an exposure range of a subject at the helical scan can be reduced. Since no X-ray cone beam is shielded, needless X-ray irradiation is not made either.

In a nineteenth aspect, the present invention provides an X-ray CT imaging method using an X-ray area detector typified by a multi-row X-ray detector or a flat panel, comprising tilting a scanning gantry in such a manner that X-ray irradiation is started in a state in which an end surface of an X-ray cone beam on the front side as viewed in a linearly-moved direction of a helical scan is set vertical or substantially vertical to the linearly-moved direction; and controlling X-ray irradiation in a such a manner that the X-ray irradiation is completed at such a number of revolutions that an end surface of the X-ray cone beam on the rear side as viewed in the linearly-moved direction of the helical scan becomes parallel or substantially parallel to a reconstruction area.

In the X-ray CT imaging method according to the nineteenth aspect, when, for example, the reconstruction area is vertical to the linearly-moved direction, the end surface on the front side as viewed in the linearly-moved direction, of the X-ray cone beam at the start of the X-ray irradiation is set vertical or substantially vertical to the linearly-moved direction owing to the scanning gantry being tilted. When, for example, the reconstruction area is vertical to the linearly-moved direction, the X-ray irradiation is completed at such an unintegral number of revolutions that the end surface on the rear side as viewed in the linearly-moved direction, of the X-ray cone beam at the completion of the X-ray irradiation becomes vertical or substantially vertical to the linearly-moved direction. Thus, no X-ray is spread to an unnecessary range at the start of the X-ray irradiation or the completion of the X-ray irradiation, and hence an exposure range of a subject at the helical scan can be reduced. Since the X-ray cone beam is not shielded, needless X-ray irradiation is not done either.

In a twentieth aspect, the present invention provides an X-ray CT imaging method according to any of the eleventh through nineteenth aspects, wherein the helical scan is a variable pitch helical scan or a variable speed helical scan.

In the above constitution, the variable pitch helical scan or the variable speed helical scan is a helical scan which collects or acquires image reconstruction data even at the start of a linear movement and the completion thereof, and even in acceleration or deceleration in its mid course.

In the X-ray CT imaging method according to the twentieth aspect, the variable pitch helical scan or the variable speed helical scan provides or produces a low speed upon the start or completion of the linear movement. Therefore, the image quality of a portion equivalent to its start or completion is improved as compared with the case of a constant pitch helical scan or a constant speed helical scan.

According to an X-ray CT apparatus and an X-ray CT imaging method of the present invention, no X-ray is spread to an unnecessary range at the start of X-ray irradiation or the completion thereof, and hence an exposure range of a subject at a helical scan can be reduced. Here, the helical scan includes a variable pitch helical scan or a variable speed helical scan. Since no X-ray cone beam is shielded, needless X-ray irradiation is not done.

An X-ray CT apparatus and an X-ray CT imaging method according to the present invention can be used for imaging a tomogram of a subject.

Further objects and advantages of the present invention will be apparent from the following description of the preferred embodiments of the invention as illustrated in the accompanying drawings.

BRIEF DESCRIPTION OF THE DRAWINGS

FIG. 3 is a flowchart depicting a schematic operation of the X-ray CT apparatus according to the embodiment 1.

FIG. 4 is an explanatory diagram showing a data structure.

FIG. 14 is a flowchart showing the details of a three-dimensional image reconstructing process.

FIG. 17 is a conceptual diagram showing a state in which projection data Dr at a view angle view=0° is projected on the reconstruction area P.

FIG. 18 is a conceptual diagram depicting backprojection pixel data D2 on the reconstruction area P at the view angle view=0°.

FIG. 19 is an explanatory diagram illustrating a state in which backprojection pixel data D2 are added over all views in association with pixels to obtain backprojection data D3.

FIG. 20 is a conceptual diagram showing a circular reconstruction area R.

DETAILED DESCRIPTION OF THE INVENTION

The present invention will hereinafter be explained in further detail according to embodiments illustrated in the accompanying drawings. Incidentally, the present invention is not limited to or by the embodiments.

Embodiment 1

Figure 1:
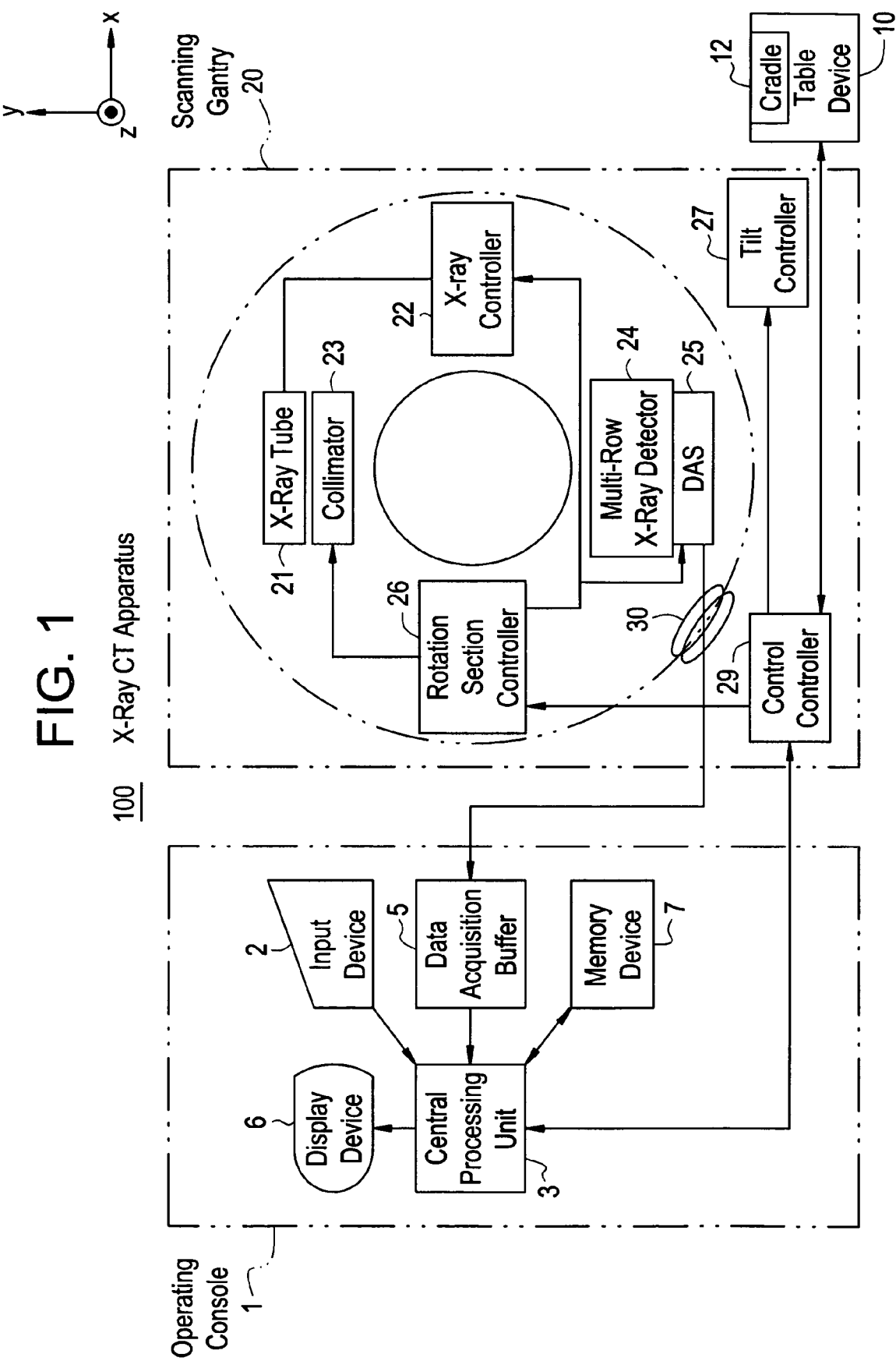
FIG. 1 is a block diagram showing an X-ray CT apparatus according to an embodiment 1.

FIG. 1 is a configurational block diagram showing an X-ray C apparatus according to an embodiment 1.

The present X-ray CT apparatus 100 is equipped with an operating console 1, a table device 10 and a scanning gantry 20.

The operating console 1 includes an input device 2 which receives an operator's input, a central processing unit 3 which executes an image reconstructing process, etc., a data acquisition buffer 5 which collects projection data obtained by the scanning gantry 20, a display device 6 which displays a CT image reconstructed from the projection data, and a memory device 7 which stores programs, data and an X-ray CT image therein.

The table device 10 includes a cradle 12 which places a subject thereon and inserts and draws it into and from a bore (cavity section). The cradle 12 is elevated and linearly moved by a motor built in the table device 10.

The scanning gantry 20 is provided with an X-ray tube 21, an X-ray controller 22, a collimator 23, a multi-row X-ray detector 24, a DAS (Data Acquisition System) 25, a rotation section controller 26 which controls an X-ray tube 21 rotated about a body axis of the subject, etc., a tilt controller 27 which performs control of the scanning gantry 20 at the time that the scanning gantry 20 is tilted forward or backward of its rotational axis, a control controller 29 which performs a transfer of a control signal or the like between the operating console 1 and the table device 10, and a slip ring 30 which transfers a power supply, a control signal and collected data.

Figure 2:
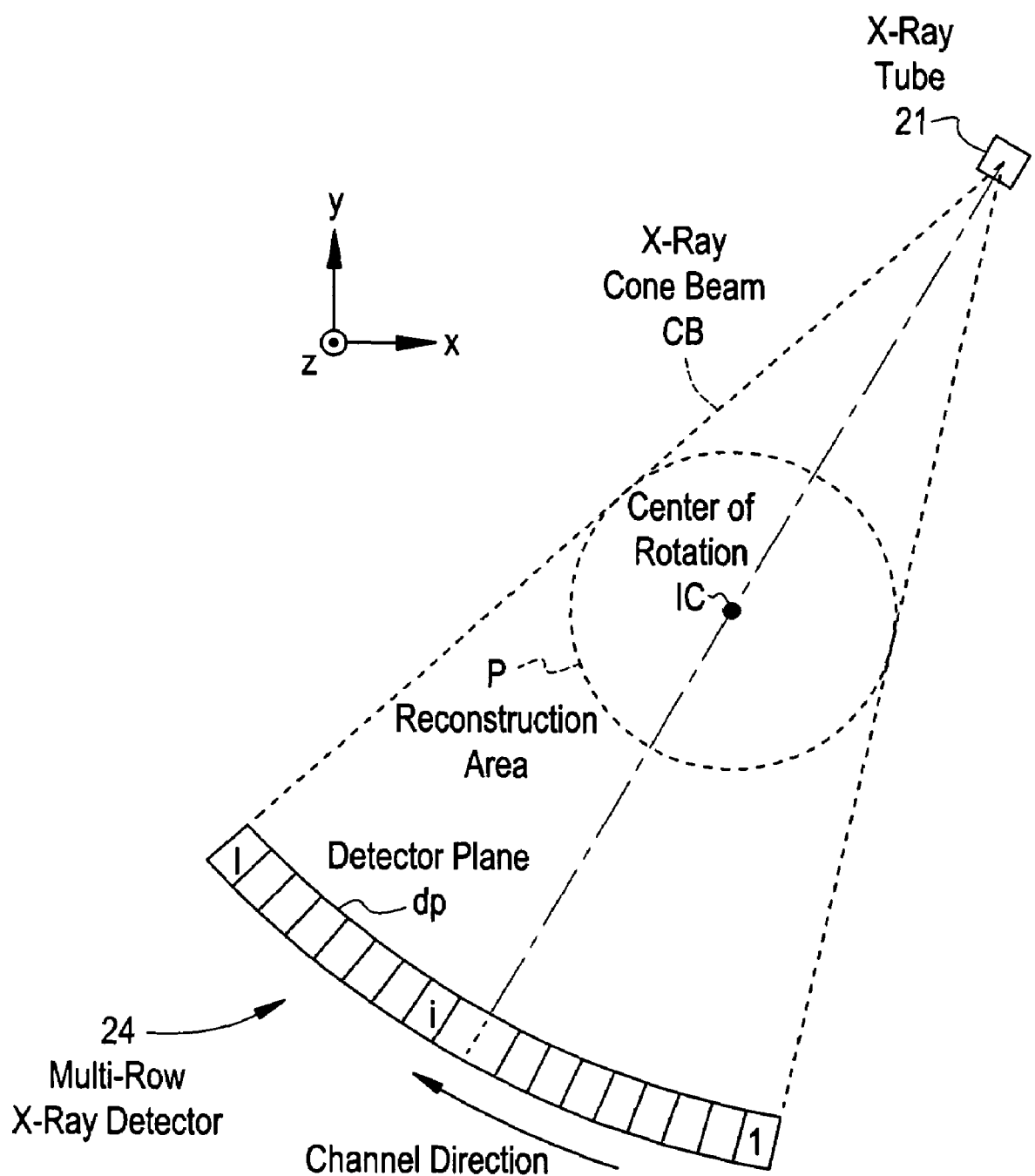
FIG. 2 is an explanatory diagram illustrating a geometrical layout of an X-ray tube and a multi-row X-ray detector.

FIG. 2 is a diagram for describing a geometrical layout of the X-ray tube 21 and the multi-row X-ray detector 24.

The X-ray tube 21 and the multi-row X-ray detector 24 are rotated about the center of rotation IC. Assuming that the vertical direction is defined as a y-axis direction, the linearly-moved direction of the cradle 12 is defined as a Z-axis direction, the direction orthogonal to the z-axis direction and the y-axis direction is defined as an x-axis direction, and a tilt angle α of the scanning gantry 20 is 0°, the plane on which the X-ray tube 21 and the multi-row X-ray detector 24 are rotated, is an xy plane.

The X-ray tube 21 generates an X-ray beam called "X-ray cone beam CB". When the direction of a central axis of the X-ray cone beam CB is parallel to the y direction, a view angle is assumed to be 0°.

The multi-row X-ray detector 24 has detector rows ranging from a first row to a jth row. For example, J is assumed to be J=256. The respective detector rows have a 1 st channel through an Ith channel. For example, I is assumed to be I=1024.

Projection data acquired with being irradiated with an X-ray are supplied from the multi-row X-ray detector 24 to the DAS 25 where they are A/D converted, after which the data are inputted to the data acquisition buffer 5 via the slip ring 30.

The projection data inputted to the data acquisition buffer 5 are processed by the central processing unit 3 in accordance with the corresponding program stored in the memory device 7, followed by being converted into a tomogram. The tomogram is displayed on the display device 6.

FIG. 3 is a flowchart showing a rough outline of the operation of the X-ray CT apparatus 100.

At Step S1, the scanning gantry 20 is inclined by a tilt angle α. Thereafter, a helical scan operation is performed while the X-ray tube 21 and the multi-row X-ray detector 24 are being rotated about the subject and the cradle 12 is being linearly moved, thereby acquiring projection data D0(view, j, i) expressed in a tilt angle α, a table linearly-moved position z, a view angle view, a detector sequence number j and a channel number i. The table linearly-moved position z is one processed by counting a z-axis direction position pulse by an encoder built in the table device 10, converting it into a z-axis coordinate by the control controller 29 and adding it to the projection data of the DAS 25 as z-axis coordinate information via the slip ring 30.

FIG. 4 shows a format of projection data at a given view angle, which are added with z-axis coordinate information at a tilt angle α.

Incidentally, this data acquisition process will be described later with reference to FIG. 10.

At Step S2, a pre-treatment including an offset correction, logarithmic transformation, an X-ray dose correction and a sensitivity correction is effected on the projection data D0(view, j, i) to obtain projection data Din(view, j, i).

At Step S3, a beam hardening process is effected on the pre-treated projection data Din(view, j, i). The beam hardening process is expressed in the following polynomial equation, for example. In the polynomial equation, $B_0$, $B_1$ and $B_2$ indicate beam hardening coefficients respectively.

$$Dout(view, j, i) = Din(view, j, i) \times (B_0(j, i) + B_1(j, i) \times Din(view, j, i) + B_2(j, i) \times Din(view, j, i)^2)$$

Since beam hardening corrections independent of one another every respective rows of the detector can be performed at this time, differences in characteristic every respective detector rows can be corrected if tube voltages of respective data acquisition systems differ according to imaging conditions.

Figure 5:
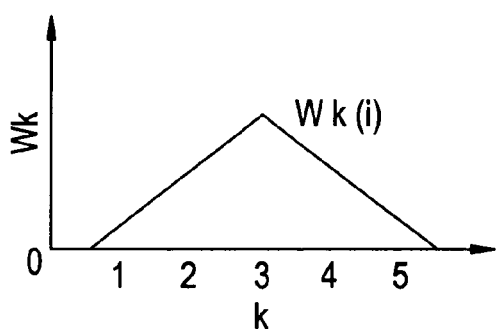
FIG. 5 is an explanatory diagram illustrating row-direction filter coefficients.

At Step S4, a Z filter convolution process for performing multiplication of a filter in a z direction (row direction) is effected on the projection data Dout(view, j, i) subjected to the beam hardening correction. That is, the projection data Dout(view, j, i) subjected to the beam hardening correction are multiplied by, for example, such row-direction filter coefficients Wk(i) as shown in FIG. 5 in the row direction to determine projection data Dcor(view, j, i).

$$Dcor(\alpha, z, \text{view}, j, i) = \sum_{k=1}^{5} (Dou(\alpha, z, \text{view}, j+k-3, i) \times Wk(i))$$

$$\text{where } \sum_{k=1}^{5} (Wk(i)) = 1$$

$Dout(\alpha, z, \text{view}, -1, i) =$ $\quad Dout(\alpha, z, \text{view}, 0, i) = Dout(\alpha, z, \text{view}, 1, i)$ $Dout(\alpha, z, \text{view}, J+1, i) =$ $\quad Dout(\alpha, z, \text{view}, J+2, i) = Dout(\alpha, z, \text{view}, J, i)$ A slice thickness can be controlled by a row-direction filter coefficient Wk(i) as a Z filter.

Figure 6:
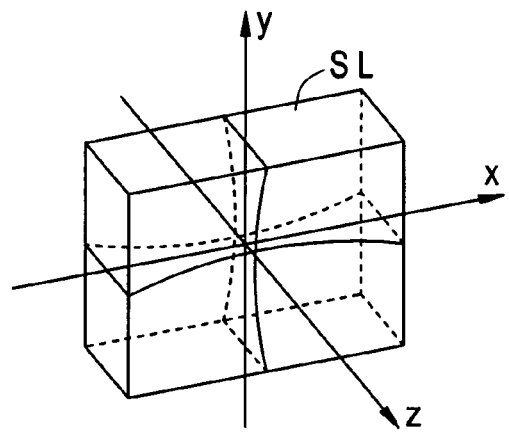
FIG. 6 is an explanatory diagram showing a slice thicker than the center of a reconstruction area in thickness at its periphery.

In a slice SL as shown in FIG. 6, its peripheral slice thickness generally becomes thicker as compared with a reconstruction center image-reconstructed.

Figure 7:
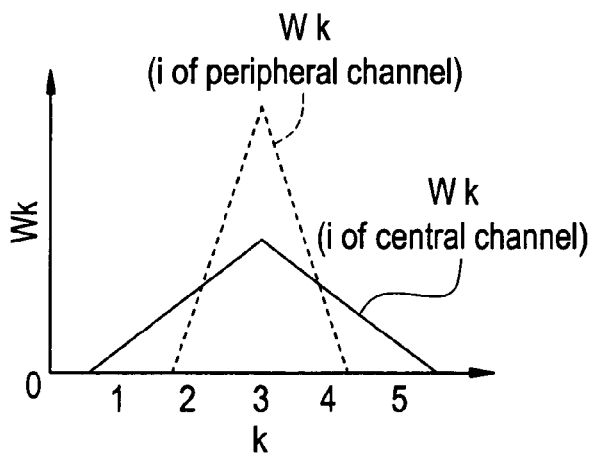
FIG. 7 is an explanatory diagram depicting row-direction filter coefficients that differ according to channels.
Figure 8:
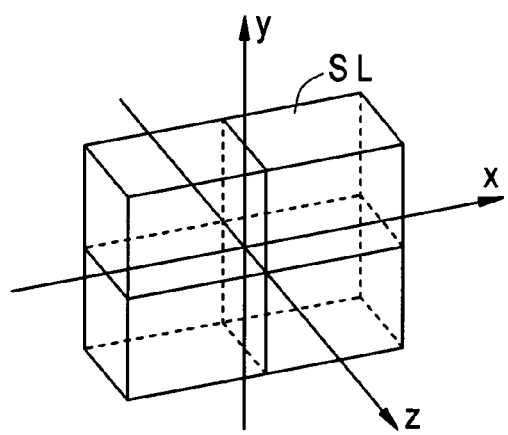
FIG. 8 is an explanatory diagram illustrating a slice uniform in thickness even at the center of a reconstruction area and its periphery.

Therefore, as shown in FIG. 7, a row-direction filter coefficient Wk (i of central channel) at which the central channel is broadly changed in width, is used, and a row-direction filter coefficient Wk (i of peripheral channel) at which the peripheral channel is narrowly changed in width, is used. Thus, it is possible to set a slice SL having a slice thickness close to uniformity even at the reconstruction center and the periphery as shown in FIG. 8.

Both Artifacts and noise are improved when the slick thickness is slightly made thick by the row-direction filter coefficients Wk(i). Consequently, the manner of an improvement in artifact and the manner of an improvement in noise can also be controlled. That is, the quality of a three-dimensional image reconstructed CT image can be controlled.

Figure 9:
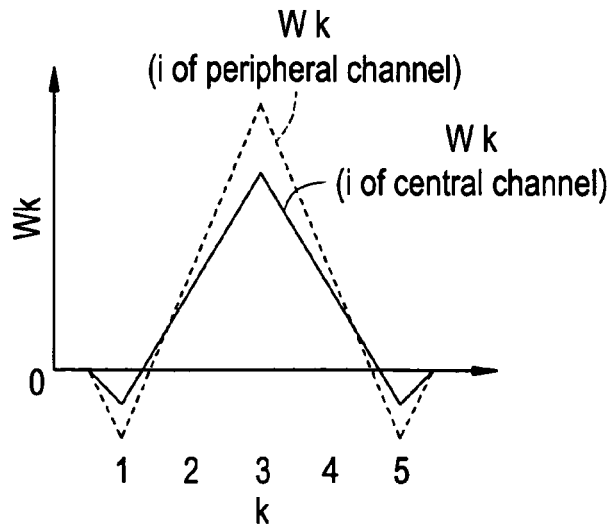
FIG. 9 is an explanatory diagram showing row-direction filter coefficients for thinning a slice thickness.

By setting the row-direction filter coefficients Wk(i) to de-convolution filters as shown in FIG. 9, a CT image having a thin slice thickness can also be realized.

Referring back to FIG. 3, a reconstruction function convolution process is carried out at Step S5. That is, a Fourier transform is performed on projection data, each of which is followed by being multiplied by a reconstruction function to perform an inverse Fourier transform thereof. Assuming that the projection data subsequent to the reconstruction function convolution process is defined as Dr(view, j, i), the reconstruction function is defined as Kernel(j), and convolution computation is expressed in *, the reconstruction function convolution process is expressed as follows:

$\quad Dr(\text{view}, j, i) = Dcor(\text{view}, j, i) * Kernel(j)$

Since the independent reconstruction function convolution process can be carried out using the reconstruction function Kernel(j) independent for each row of the detector, differences in noise and resolution characteristics every respective detector rows can be corrected.

At Step S6, a three-dimensional back projecting process is effected on the projection data Dr(view, j, i) to determine backprojected data D3(x, y). The three-dimensional back projecting process will be explained later with reference to FIG. 17.

At Step S7, a post-treatment such as an image filter convolution process, a CT value converting process or the like is effected on the backprojected data D3(x, y) to obtain a CT image.

Assuming that data subsequent to the image filter convolution process is defined as D4(x, y), a detector row number corresponding to a central pixel of the CT image is defined as j, and an image filter is defined as Filter(x, y), the image filter convolution process is expressed as follows:

$\quad D4(x, y) = D3(x, y) * Filter(x, y)$

That is, since the image filter convolution process independent for each slice position of the CT image can be carried out, differences in noise and resolution characteristics every slice positions can be corrected.

Figure 10:
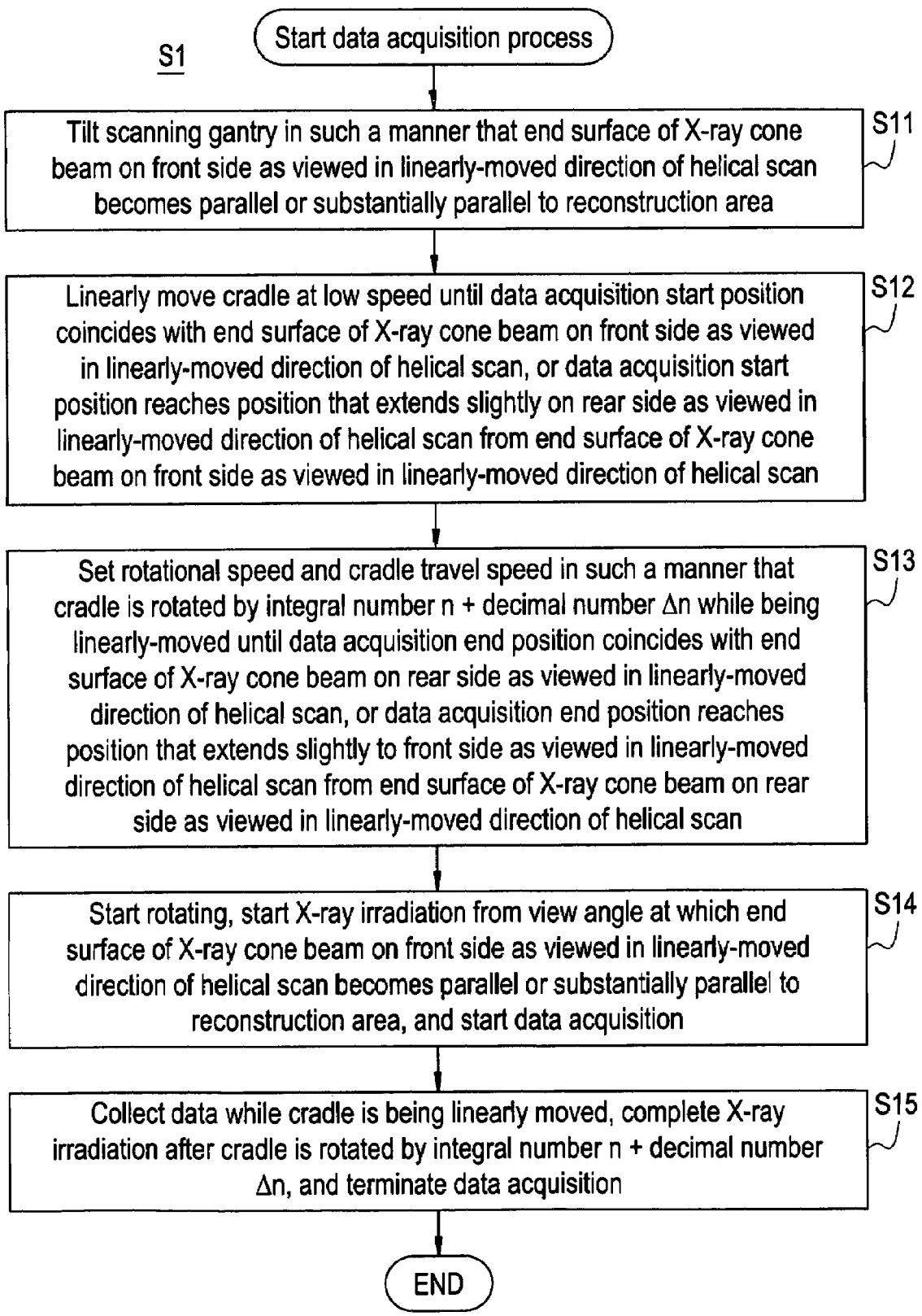
FIG. 10 is a flowchart depicting the details of a data acquisition process.

FIG. 10 is a flowchart showing the details of the data acquisition process (Step S1 of FIG. 3).

Figure 11:
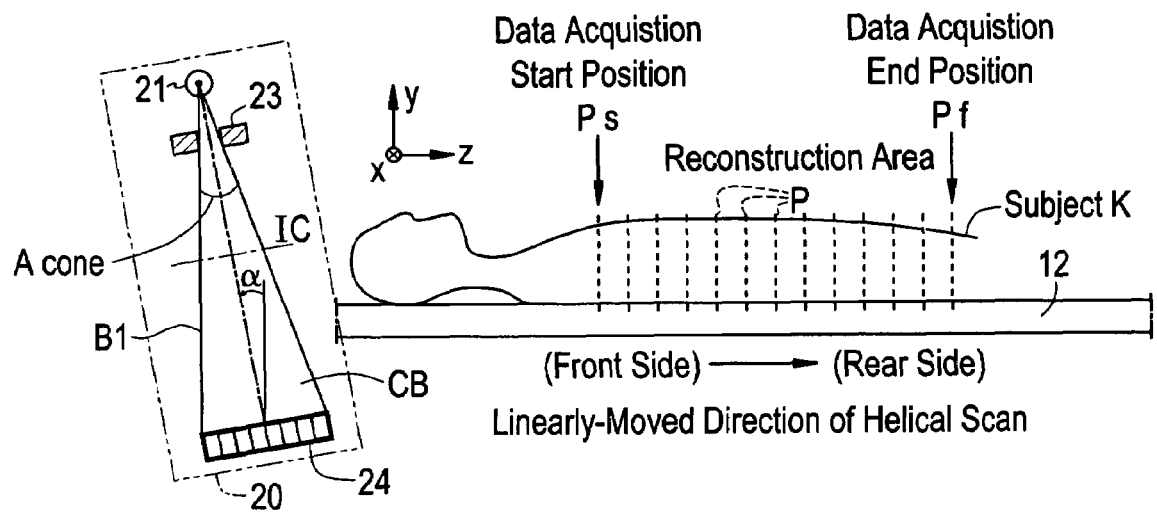
FIG. 11 is a conceptual diagram showing a state in which a scanning gantry is tilted in accordance with a reconstruction area parallel to an xy plane.

At Step S11, as shown in FIG. 11, the scanning gantry 20 is tilted in such a manner that an end surface B1 of an X-ray cone beam CB on the front side as viewed in a linearly-moved direction of a helical scan becomes parallel or substantially parallel to a reconstruction area P.

Now, FIG. 11 shows a case in which the reconstruction area P is parallel to the xy plane. Assuming that an X-ray cone beam angle spread in the linearly-moved direction of the helical scan is Acone, the scanning gantry 20 is tilted by Acone/2 or a tilt angle α close to it.

Figure 12:
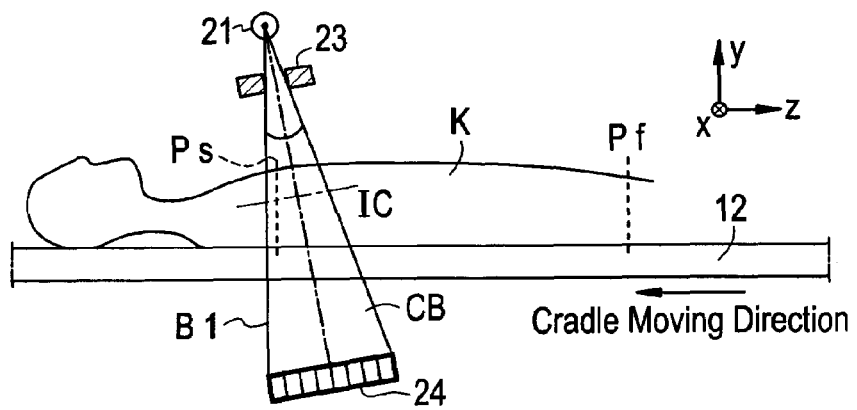
FIG. 12 is a conceptual-diagram graph illustrating a state at the start of data acquisition.

At Step S12, as shown in FIG. 12, the cradle 12 is linearly moved at low speed until a data acquisition start position Ps coincides with the end surface B1 of the X-ray cone beam CB on the front side as viewed in the linearly-moved direction of the helical scan, or the data acquisition start position Ps reaches a position that extends slightly on the rear side as viewed in the linearly-moved direction of the helical scan. Incidentally, the linearly-moved direction of the helical scan and the direction of movement of the cradle 12 are placed in a reverse relationship.

Figure 13:
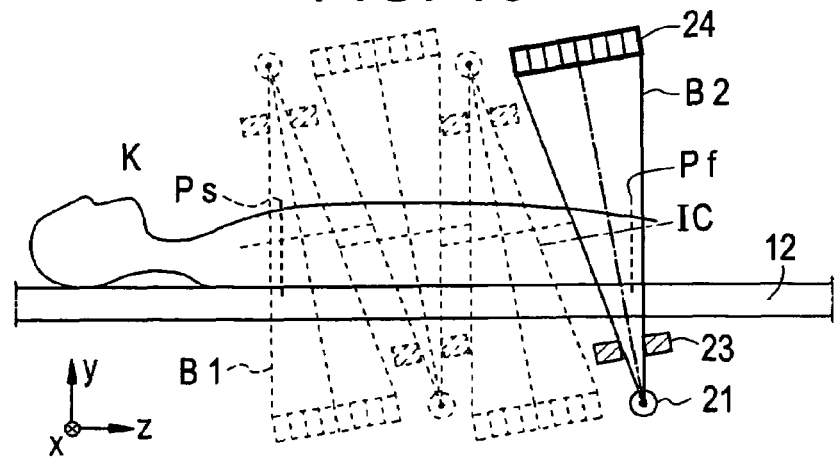
FIG. 13 is a conceptual-diagram graph showing a state at the completion of data acquisition.

At Step S13, as shown in FIG. 13, a rotational speed and a cradle travel speed are set in such a manner that the cradle 12 is rotated by an integral number n+a decimal number Δn while the cradle 12 is being linearly-moved until a data acquisition end position Pf coincides with an end surface B2 of the X-ray cone beam CB on the rear side as viewed in the linearly-moved direction of the helical scan, or the data acquisition end position Pf reaches a position that extends slightly to the front side as viewed in the linearly-moved direction of the helical scan.

Although FIG. 13 shows a case in which Δn=0.5 here, the decimal number is not limited to it. The decimal number may be Δn=0.25 or Δn=0.75, for example.

At Step S14, the rotation of the scanning gantry 20 is started. X-ray irradiation is started from a view angle at which the end surface B1 of the X-ray cone beam CB on the front side as viewed in the linearly-moved direction of the helical scan becomes parallel or substantially parallel to the reconstruction area, and data acquisition is started.

At Step S15, projection data D0(α, z, view, j, i) are collected while the cradle 12 is being linearly moved. After the cradle 12 is rotated by the integral number n+decimal number Δn, the X-ray irradiation is completed and thereafter the data acquisition is terminated.

FIG. 14 is a flowchart showing the details of the three-dimensional back projecting process (Step S6 of FIG. 3).

Although the reconstruction area P is set parallel to the xy plane for convenience of explanation, this process is similar even where the reconstruction area P is tilted by θ from the xy plane.

At Step S61, attention is paid to one of all views (i.e., views corresponding to 360° or views corresponding to "180°+fan angle") necessary to reconstruct the CT image. Projection data Dr corresponding to respective pixels of a reconstruction area R are extracted.

Figure 15A:
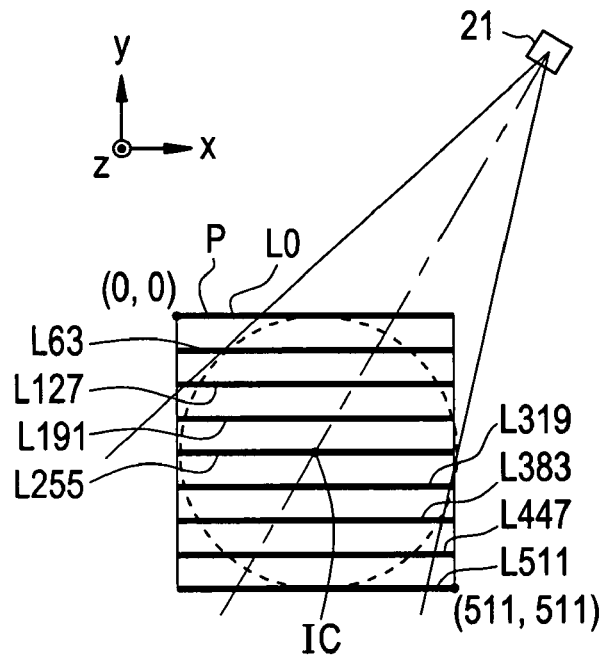
FIG. 15 is a conceptual diagram showing a state in which pixel rows on a reconstruction area P are projected in an X-ray penetration direction.
Figure 15B:
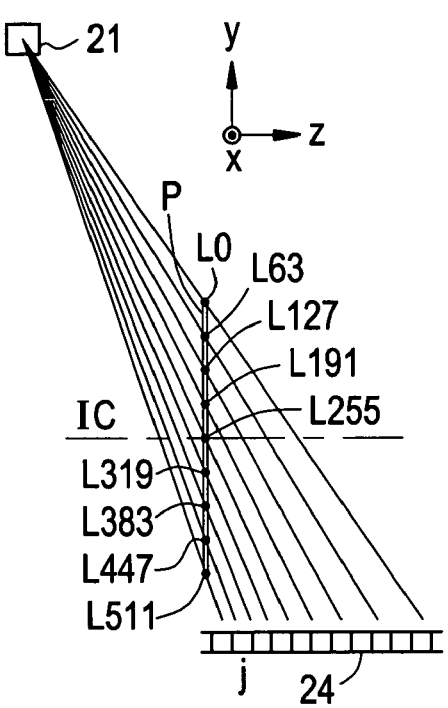
Figure 16:
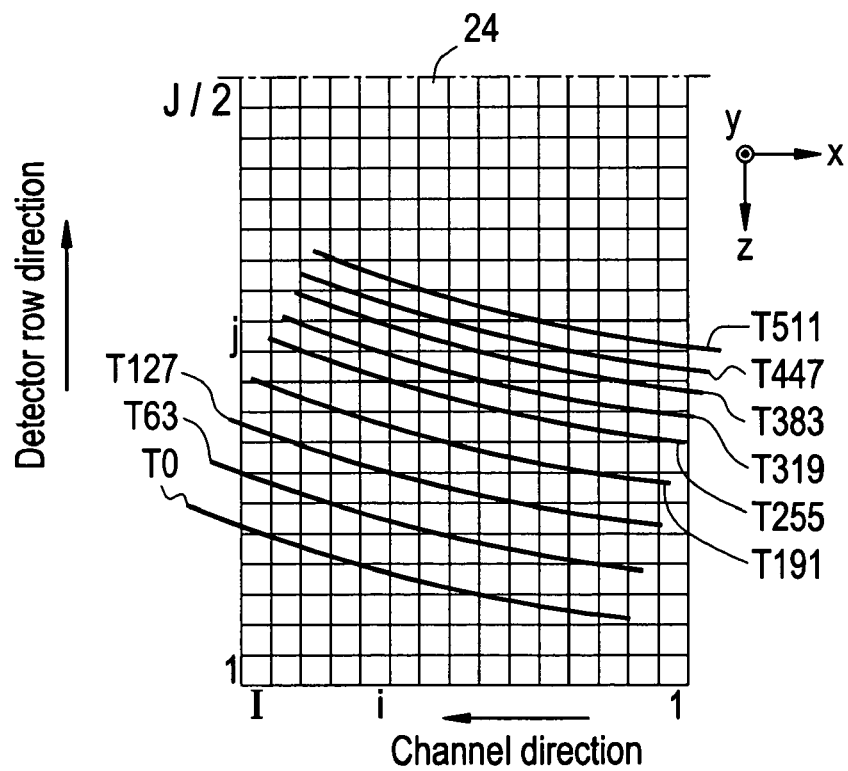
FIG. 16 is a conceptual diagram illustrating lines formed by projecting the pixel rows on the reconstruction area P onto a detector surface or plane.

As shown in FIG. 15, a square reconstruction area P of 512×512 pixels, which is parallel to an xy plane, is considered. A pixel row L0 parallel to an x axis of y=0, a pixel row L63 of y=63, a pixel row L127 of y=127, a pixel row L191 of y=191, a pixel row L255 of y=255, a pixel row L319 of y=319, a pixel row L383 of y=383, a pixel row L447 of y=447, and a pixel row L511 of y=511 are taken by way of example. If projection data D0 on lines T0 through T511 shown in FIG. 16, which are obtained by projecting these pixel rows L0 through L511 onto the surface of the multi-row X-ray detector 24 in an X-ray penetration direction, are extracted, they result in projection data Dr corresponding to the pixel rows L0 through L511.

The X-ray penetration direction is determined depending upon geometrical positions of an X-ray focal point of the X-ray tube 21, the respective pixels and the multi-row X-ray detector 24. Since, however, the z coordinates of the projection data D0(view, j, i) are already known, the X-ray penetration direction can be accurately determined even in the case of the projection data D0(view, j, i) being in acceleration/deceleration.

When part of each line falls outside the surface of the multi-row X-ray detector 24 as in the case of, for example, the line T0 obtained by projecting the pixel row L0 onto the surface of the multi-row X-ray detector 24 in the X-ray penetration direction, its corresponding projection data Dr is set to "0".

Thus, projection data Dr(view, x, y) corresponding to the respective pixels of the reconstruction area P can be extracted as shown in FIG. 17.

Referring back to FIG. 14, at Step S62, the projection data Dr(view, x, y) are multiplied by cone beam reconstruction weighting factors or coefficients to create projection data D2(view, x, y) shown in FIG. 18.

Now, the cone beam reconstruction weighting factors are as follows:

Assuming that in the case of a fan beam image reconstruction, the angle which a straight line connecting the focal point of the X-ray tube 21 and a pixel g(x, y) on the reconstruction area P forms with a central axis Bc of an X-ray beam at view=βa, is taken as γ, and an opposite view thereof is taken as view=βb, βb is expressed as follows:

$$\beta b = \beta a + 180° - 2\gamma$$

Assuming that the angles which the X-ray beam passing through the pixel g(x, y) on the reconstruction area P and its opposite X-ray beam form with the reconstruction area P, are taken as αa and αb, the corresponding backprojected data are multiplied by cone beam reconstruction weighting factors ωa and ωb dependent on these angles αa and αb and then added together to determine backprojected data D2(0, x, y).

$$D2(0, x, y) = \omega a \cdot D2(0, x, y)\_a + \omega b \cdot D2(0, x, y)\_b$$

where D2(0, x, y)_a: projection data at a view βa, and D2(0, x, y)_b: projection data at a view βb.

Incidentally, the sum of the cone beam reconstruction weighting factors ωa and ωb for the X-ray beam and its opposite X-ray beam is expressed as follows:

$$\omega a + \omega b = 1$$

Multiplying the data by the cone beam reconstruction weighting factors ωa and ωb and adding them together as described above makes it possible to reduce cone angle artifacts.

As the cone beam reconstruction weighting factors ωa and ωb, for example, ones determined from the following equations can be used.

When a fan beam angle is assumed to be γmax with f( ) as a function, the following are given:

$$ga = f(\pi + \gamma max - |\beta a|, |\tan(\alpha a)|)$$

$$gb = f(\pi + \gamma max - |\beta b|, |\tan(\alpha b)|)$$

$$xa = 2 \cdot ga^q / (ga^q + gb^q)$$

$$xb = 2 \cdot gb^q / (ga^q + gb^q)$$

$$\omega a = xa^2 \cdot (3 - 2xa)$$

$$\omega b = xb^2 \cdot (3 - 2xb)$$

Let's assume that, for example, f( )=max( ): function that takes a large value, and q=1.

In the case of the fan beam image reconstruction, each pixel on the reconstruction area P is further multiplied by a distance coefficient. When the distance from the focal point of the X-ray tube 21 to each of a detector row j and a channel i of the multi-row X-ray detector 24 corresponding to the projection data Dr is assumed to be r0, and the distance from the focal point of the X-ray tube 21 to the corresponding pixel on the reconstruction area P corresponding to the projection data Dr, is assumed to be r1, the distance coefficient is expressed in $(r1/r0)^2$.

A parallel beam image reconstruction is similar to the fan beam image reconstruction if βb=βa+180°.

At Step S63, as shown in FIG. 19, projection data D2(view, x, y) are added to pre-cleared backprojected data D3(x, y) in association with pixels.

At Step S64, Steps S61 through S63 are repeated with respect to all views (i.e., views corresponding to 360° or views corresponding to "180°+fan angle") necessary to reconstruct the CT image to obtain the backprojected data D3(x, y) as shown in FIG. 19.

Incidentally, the reconstruction area P may be configured as a circular area as shown in FIG. 20.

According to the X-ray CT apparatus 100 of the embodiment 1, the X-ray is not spread to the front and rear sides as viewed in the linearly-moved direction of the helical scan (including a variable pitch helical scan or a variable speed helical scan) rather than its linearly moved range in which one desires to collect the projection data D0. It is therefore possible to reduce a range in which a subject K is exposed to radiation. Here, the helical scan contains the variable pitch helical scan or the variable speed helical scan. Since the X-ray cone beam CB is not shielded, needless X-ray radiation is not done either. This brings about a large effect particularly when the number of revolutions "n+Δn" for the helical scan is low.

Incidentally, the image reconstructing method may be a three-dimensional image reconstructing method based on the conventionally known Feldkamp method. Further, a three-dimensional image reconstructing method proposed in each of Japanese Patent Application Nos. 2003-334188, 2004-41675, 2004-41674, 2004-73360, 2003-159244 and 2004-41675 may be used.

By convolving row-direction (z-direction) filters different in coefficient every respective detector rows, the difference in image quality due to the difference in X-ray cone angle or the like is adjusted in a conventional scan (axial scan) in particular, and the slice thickness, artifacts and noise's image quality uniform for each row are realized. However, even though it is not done, a similar effect can be brought about.

Although the tilt angle α of the scanning gantry 20 is set to Acone/2 in the embodiment 1, a similar effect can be brought about if a tilt close to it is given.

Although the number of revolutions for the X-ray irradiation data acquisition, of the scanning gantry 20 is set to the "integral number n+0.5" in the embodiment 1, a similar effect can be brought about if the number of revolutions close to it is given.

In such a variable pitch helical scan mode that a helical scan is moved forward and backward alternately over a given restricted narrow range, a further larger exposure-to-radiation reducing effect can be brought about.

Embodiment 2

While the X-ray is being set so as not to spread to both the front and rear sides as viewed in the linearly-moved direction of the helical scan rather than its linearly moved range in which one desires to collect the projection data D0, the range in which the subject K is exposed to radiation, can be reduced even by simply avoiding the spread of the X-ray to either one of the front and rear sides.

Embodiment 3

In a manner similar to the above, the present invention can be applied even to an X-ray CT apparatus using an X-ray area detector typified by a flat panel in place of the multi-row X-ray detector 24.

Embodiment 4

Figure 21:
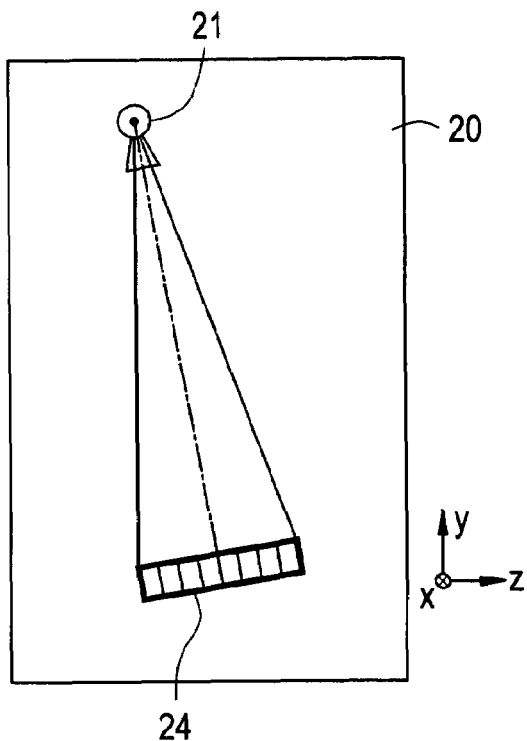
FIG. 21 is a conceptual diagram illustrating a scanning gantry of an X-ray CT apparatus according to an embodiment 4.

As shown in FIG. 21, the present invention can be implemented even as an X-ray CT apparatus having a scanning gantry 20 wherein an X-ray tube 21 and a multi-row X-ray detector 24 are fixedly tilted, and X-ray irradiation is started in a state in which an end surface of an X-ray cone beam on the front side as viewed in a linearly-moved direction of a helical scan is set vertical or substantially vertical. In this case, the central axis of rotation is also tilted. However, the central axis of rotation may be set horizontal, or tilting and horizontalization may switchably be set.

Embodiment 5

Figure 22:
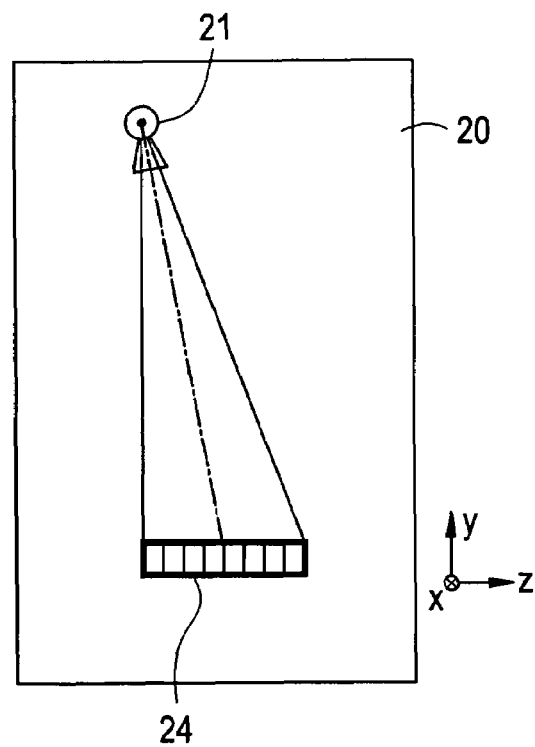
FIG. 22 is a conceptual diagram showing a scanning gantry of an X-ray CT apparatus according to an embodiment 5.

As shown in FIG. 22, the present invention can be implemented even as an X-ray CT apparatus having a scanning gantry 20 wherein an X-ray tube 21 is fixedly tilted, and X-ray irradiation is started in a state in which an end surface of an X-ray cone beam on the front side as viewed in a linearly-moved direction of a helical scan is set vertical or substantially vertical. In this case, the central axis of rotation is set horizontal. However, the central axis of rotation may be tilted. Alternatively, horizontalization and tilting may be set switchable.

Many widely different embodiments of the invention may be configured without departing from the spirit and the scope of the present invention. It should be understood that the present invention is not limited to the specific embodiments described in the specification, except as defined in the appended claims.

The invention claimed is:

1. An X-ray CT apparatus comprising:
an X-ray area detector comprising one of a multi-row detector and a flat panal;
a scanning gantry; and
a scanning gantry tilting device configured to tilt the scanning gantry such that X-ray irradiation is started in a state in which an end surface of an X-ray cone beam on front side as viewed in a linearly-moving direction of a helical scan is rendered parallel or substantially parallel to a reconstruction area, said reconstruction area set perpendicular to the linearly-moving direction, wherein the scanning gantry tilting device tilts the scanning gantry such that X-ray irradiation is performed in such a manner that the number of revolutions during an X-ray irradiation period at a helical scan reaches "n+n" (where n: integral number and n: decimal number).

2. An X-ray CT apparatus comprising:
an X-ray area detector comprising one of a multi-row detector and a flat panal;
an X-ray irradiating device which forms an X-ray cone beam in such a manner that X-ray irradiation is started in a state in which an end surface of the X-ray cone beam on a front side as viewed in a linearly-moving direction of a helical scan is set vertical or substantially vertical to the linearly-moving direction, wherein the X-ray irradiation is performed in such a manner that the number of revolutions during an X-ray irradiation period at a helical scan reaches "n+n" (where n: integral number and n: decimal number).

3. An X-ray CT apparatus comprising:
an X-ray area detector comprising one of a multi-row detector and a flat panal; and
an X-ray irradiation control device which controls X-ray irradiation in such a manner that the number of revolutions during an X-ray irradiation period at a helical scan reaches "n +n" (where n: integral number and n: decimal number), and which controls the X-ray irradiation of an X-ray cone beam in such a manner that X-ray irradiation is started in a state in which an end surface of the X-ray cone beam on a front side as viewed in a linearly-moving direction of the helical scan is rendered horizontal or substantially horizontal to a reconstruction area, said reconstruction area set vertical to the linearly-moving direction.

4. An X-ray CT apparatus comprising:
an X-ray area detector comprising one of a multi-row detector and a flat panal;
a scanning gantry tilting device which tilts a scanning gantry upon a helical scan; and
an X-ray irradiation control device which controls X-ray irradiation in such a manner that the number of revolutions during an X-ray irradiation period at the helical scan reaches "n+n" (where n: integral number and n: decimal number), and which controls the X-ray irradiation of an X-ray cone beam in such a manner that X-ray irradiation is started in a state in which an end surface of an X-ray cone beam on a front side as viewed in a linearly-moving direction of the helical scan is rendered horizontal or substantially horizontal to a reconstruction area, said reconstruction area set vertical to the linearly-moving direction.

5. An X-ray CT apparatus according to claim 1, wherein when an X-ray cone beam angle spread in the linearly-moving direction is assumed to be Acone, the scanning gantry is tilted by Acone/2 or an angle close thereto.

6. An X-ray CT apparatus according to claim 3, wherein n=0.5 or a value close thereto.

7. An X-ray CT apparatus according to claim 1, further comprising a three-dimensional image reconstructing device or an X-ray cone beam image reconstructing device.

8. An X-ray CT apparatus comprising:
an X-ray area detector comprising one of a multi-row detector and a flat panal; and
a scanning gantry tilting device which tilts a scanning gantry in such a manner that X-ray irradiation is completed in a state in which an end surface of an X-ray cone beam on a rear side as viewed in a linearly-moving direction of a helical scan is set parallel or substantially parallel to a reconstruction area, said reconstruction area set vertical to the linearly-moving direction, wherein the scanning gantry tilting device tilts the scanning gantry such that the X-ray irradiation is performed in such a manner that the number of revolutions during an X-ray irradiation period at a helical scan reaches "n+n" (where n: integral number and n: decimal number).

9. An X-ray CT apparatus comprising:
an X-ray area detector comprising one of a multi-row detector and a flat panal;
a scanning gantry tilting device which tilts a scanning gantry in such a manner that X-ray irradiation is started in a state in which an end surface of an X-ray cone beam on a front side as viewed in a linearly-moving direction of a helical scan is set vertical or substantially vertical to the linearly-moving direction; and
an X-ray irradiation control device which controls X-ray irradiation in a such a manner that the X-ray irradiation is completed at such a number of revolutions that an end surface of the X-ray cone beam on a rear side as viewed in the linearly-moving direction of the helical scan becomes parallel or substantially parallel to a reconstruction area said reconstruction area set vertical to the linearly-moving direction.

10. An X-ray CT apparatus according to claim 1, further comprising a helical scan device which performs a variable pitch helical scan or variable speed helical scan.

11. An X-ray CT imaging method using an X-ray area detector comprising one of a multi-row detector and a flat panal, comprising:
tilting a scanning gantry in such a manner that X-ray irradiation is started n a state in which an end surface of an X-ray cone beam on a front side as viewed in a linearly-moving direction of a helical scan is set parallel or substantially parallel to a reconstructing area, said reconstruction area set vertical to the linearly-moving direction, wherein the scan in gantry is tilted such that the X-ray irradiation is performed in such a manner that the number of revolutions during an X-ray irradiation period at a helical scan reaches "n+n" (where n: integral number and n: decimal number).

12. An X-ray CT imaging method using an X-ray area detector comprising one of a multi-row detector and a flat panal, comprising:
forming an X-ray cone beam in such a manner that X-ray irradiation is started in a state in which an end surface of the X-ray cone beam on a front side as viewed i a linearly-moving direction of a helical scan is set vertical or substantially vertical to the linearly-moving direction, wherein the X-ray irradiation is performed in such a manner that the number of revolutions during an X-ray irradiation period at a helical scan reaches "n+n" (where n: integral number and n: decimal number).

13. An X-ray CT imaging method using an X-ray area detector comprising one of a multi-row detector and a flat panal, comprising:
controlling X-ray irradiation in such a manner that the number of revolutions during an X-ray irradiation period at a helical scan reaches "n+n" (where n: integral number and n: decimal number), and controlling the X-ray irradiation of an X-ray cone beam in such a manner that X-ray irradiation is started in a state in which an end surface of an X-ray cone beam on a front side as viewed in a linearly-moving direction of the helical scan is rendered horizontal or substantially horizontal to a reconstruction area, said reconstruction area set vertical to the linearly-moving direction.

14. An X-ray CT imaging method using an X-ray area detector comprising one of a multi-row detector and a flat panal, comprising:
tilting a scanning gantry upon a helical scan; and
controlling X-ray irradiation in such a manner that the number or revolutions during an X-ray irradiation period at the helical scan reaches "n+n" (where n: integral number and n: decimal number), and controlling the X-ray irradiation of an X-ray cone beam in such a manner that X-ray irradiation is started in a state in which an end surface of an X-ray cone beam on a front side as viewed in a linearly-moving direction of the helical scan s rendered horizontal or substantially horizontal to a reconstruction area, said reconstruction area set vertical to the linearly-moving direction.

15. An X-ray CT imaging method using an X-ray area detector comprising one of a multi-row detector and a flat panal, comprising:
tilting a scanning gantry in such a manner that X-ray irradiation is completed in a state in which an end surface of an X-ray cone beam on a rear side as viewed in linearly-moving direction of a helical scan is set parallel or substantially parallel to a reconstruction area, said reconstruction area set vertical to the linearly-moving direction wherein the scanning gantry is tilted such that the X-ray irradiation is performed in such a manner that the number of revolutions during an X-ray irradiation period at a helical scan reaches "n+n" (where n: integral number and n: decimal number).

16. An X-ray CT imaging method using an X-ray area detector comprising one of a multi-row detector and a flat panal, comprising:
tilting a scanning gantry in such a manner that X-ray irradiation is started in a state in which an end surface of an X-ray cone beam on a front side as viewed in a linearly-moving direction of a helical scan is set vertical or substantially vertical to the linearly-moving direction; and
controlling X-ray irradiation in a such a manner that the X-ray irradiation is completed at such a number of revolutions that an end surface of the X-ray cone beam on a rear side as viewed in the linearly-moving direction of the helical scan becomes parallel or substantially parallel to a reconstruction area, said reconstruction area set vertical to the linearly-moving direction.

17. An X-ray CT apparatus according to claim 4, wherein when an X-ray cone beam angle spread in the linearly-moving direction is assumed to be Acone, the scanning gantry is tilted by Acone/2 or an angle close thereto.

18. An X-ray CT apparatus according to claim 4, wherein n=0.5 or a value close thereto.

19. An X-ray CT apparatus according to claim 2, further comprising a three-dimensional image reconstructing device or an X-ray cone beam image reconstructing device.

20. An X-ray CT apparatus according to claim 3, further comprising a three-dimensional image reconstructing device or an X-ray cone beam image reconstructing device.

21. An X-ray CT apparatus according to claim 4, further comprising a three-dimensional image reconstructing device or an X-ray cone beam image reconstructing device.

22. An X-ray CT apparatus according to claim 2, further comprising a helical scan device which performs a variable pitch helical scan or variable speed helical scan.

23. An X-ray CT apparatus according to claim 3, further comprising a helical scan device which performs a variable pitch helical scan or variable speed helical scan.

24. An X-ray CT apparatus according to claim 4, further comprising a helical scan device which performs a variable pitch helical scan or variable speed helical scan.

25. An X-ray CT apparatus according to claim 8, further comprising a helical scan device which performs a variable pitch helical scan or variable speed helical scan.

26. An X-ray CT apparatus according to claim 9, further comprising a helical scan device which performs a variable pitch helical scan or variable speed helical scan.

* * * * *

UNITED STATES PATENT AND TRADEMARK OFFICE
CERTIFICATE OF CORRECTION

PATENT NO. : 7,379,526 B2
APPLICATION NO. : 11/266534
DATED : May 27, 2008
INVENTOR(S) : Nishide et al.

It is certified that error appears in the above-identified patent and that said Letters Patent is hereby corrected as shown below:

In Claim 1, column 16, line 15, delete "on front" and insert therefor -- on a front --.
In Claim 1, column 16, line 23, delete ""n + n"" and insert therefor -- "n + $\Delta$n" --.
In Claim 1, column 16, beginning on line 23, delete "n: decimal" and insert therefor -- $\Delta$n: decimal --.
In Claim 2, column 16, line 36, delete ""n + n"" and insert therefor -- "n + $\Delta$n" --.
In Claim 2, column 16, line 37, delete "n: decimal" and insert therefor -- $\Delta$n: decimal --.
In Claim 3, column 16, line 44, delete ""n + n"" and insert therefor -- "n + $\Delta$n" --.
In Claim 3, column 16, beginning on line 44, delete "n: decimal" and insert therefor -- $\Delta$n: decimal --.
In Claim 4, column 16, line 61, delete ""n + n"" and insert therefor -- "n + $\Delta$n" --.
In Claim 4, column 16, beginning on line 61, delete "n: decimal" and insert therefor -- $\Delta$n: decimal --.
In Claim 6, column 17, line 8, delete "n=0.5" and insert -- $\Delta$n=0.5 --.
In Claim 8, column 17, line 26, delete ""n + n"" and insert therefor -- "n + $\Delta$n" --.
In Claim 8, column 17, line 27, delete "n: decimal" and insert therefor -- $\Delta$n: decimal --.
In Claim 9, column 17, line 43, delete "area said" and insert therefor -- area, said --.
In Claim 10, column 17, line 47, delete "or variable" and insert therefor -- or a variable --.
In Claim 11, column 17, line 52, delete "started n" and insert therefor -- started in --.
In Claim 11, column 17, line 55, delete "reconstructing" and insert therefor -- reconstruction --.
In Claim 11, column 17, line 57, delete "scan in" and insert therefor -- scanning --.

UNITED STATES PATENT AND TRADEMARK OFFICE
CERTIFICATE OF CORRECTION

| | |
|---|---|
| PATENT NO. | : 7,379,526 B2 |
| APPLICATION NO. | : 11/266534 |
| DATED | : May 27, 2008 |
| INVENTOR(S) | : Nishide et al. |

It is certified that error appears in the above-identified patent and that said Letters Patent is hereby corrected as shown below:

In Claim 11, column 17, line 60, delete ""n + n"" and insert therefor -- "n + $\Delta$n" --.

In Claim 11, column 17, line 61, delete "n: decimal" and insert therefor -- $\Delta$n: decimal --.

In Claim 12, column 17, line 67, delete "viewed i a" and insert therefor -- viewed in a --.

In Claim 12, column 18, line 5, delete ""n + n"" and insert therefor -- "n + $\Delta$n" --.

In Claim 12, column 18, line 6, delete "n: decimal" and insert therefor -- $\Delta$n: decimal --.

In Claim 13, column 18, line 12, delete ""n + n"" and insert therefor -- "n + $\Delta$n" --.

In Claim 13, column 18, line 13, delete "n: decimal" and insert therefor -- $\Delta$n: decimal --.

In Claim 14, column 18, line 27, delete ""n + n"" and insert therefor -- "n + $\Delta$n" --.

In Claim 14, column 18, line 28, delete "n: decimal" and insert therefor -- $\Delta$n: decimal --.

In Claim 14, column 18, line 33, delete "scan s" and insert therefor -- scan is --.

In Claim 15, column 18, line 42, delete "in linearly-moving" and insert therefor -- in a linearly-moving --.

In Claim 15, column 18, line 45, delete "direction wherein" and insert therefor -- direction, wherein --.

In Claim 15, column 18, line 48, delete ""n + n"" and insert therefor -- "n + $\Delta$n" --.

In Claim 15, column 18, line 49, delete "n: decimal" and insert therefor -- $\Delta$n: decimal --.

In Claim 18, column 19, line 4, delete "n=0.5" and insert therefor -- $\Delta$n=0.5 --.

In Claim 22, column 19, line 16, delete "or variable" and insert therefor -- or a variable --.

In Claim 23, column 20, line 3, delete "or variable" and insert therefor -- or a variable --.

In Claim 24, column 20, line 6, delete "or variable" and insert therefor -- or a variable --.

UNITED STATES PATENT AND TRADEMARK OFFICE
CERTIFICATE OF CORRECTION

PATENT NO. : 7,379,526 B2
APPLICATION NO. : 11/266534
DATED : May 27, 2008
INVENTOR(S) : Nishide et al.

It is certified that error appears in the above-identified patent and that said Letters Patent is hereby corrected as shown below:

In Claim 25, column 20, line 9, delete "or variable" and insert therefor -- or a variable --.
In Claim 26, column 20, line 12, delete "or variable" and insert therefor -- or a variable --.

Signed and Sealed this

Twenty-third Day of September, 2008

JON W. DUDAS
*Director of the United States Patent and Trademark Office*